United States Patent
Atarashi et al.

[11] Patent Number: 6,162,469
[45] Date of Patent: Dec. 19, 2000

[54] MEDICAL POWDER

[75] Inventors: Takafumi Atarashi, Tokyo; Katsuto Nakatsuka, Miyagi, both of Japan

[73] Assignees: Nittetsu Mining Co., Ltd., Tokyo; Katsuta Nakatsuka, Miyagi, both of Japan

[21] Appl. No.: 09/202,052

[22] PCT Filed: Jun. 6, 1997

[86] PCT No.: PCT/JP97/01938

§ 371 Date: Mar. 29, 1999

§ 102(e) Date: Mar. 29, 1999

[87] PCT Pub. No.: WO97/47322

PCT Pub. Date: Dec. 18, 1997

[30] Foreign Application Priority Data

Jun. 10, 1996 [JP] Japan ................................ 8-147416

[51] Int. Cl.[7] ............................ A01N 59/16; A01N 59/06
[52] U.S. Cl. ........................ 424/617; 424/646; 424/655; 424/682; 424/688; 424/691
[58] Field of Search ..................... 424/646, 617, 424/655, 682, 688, 691

[56] References Cited

U.S. PATENT DOCUMENTS 5,034,145  7/1991  Leising et al. ...................... 252/62.54

FOREIGN PATENT DOCUMENTS

| | | |
|---|---|---|
| 0361797 | 4/1990 | European Pat. Off. . |
| 0546939 | 6/1993 | European Pat. Off. . |
| 89/03675 | 5/1989 | WIPO . |
| 91/09678 | 7/1991 | WIPO . |
| 93/26019 | 12/1993 | WIPO . |
| 94/21240 | 9/1994 | WIPO . |
| 96/02235 | 2/1996 | WIPO . |
| 96/09840 | 4/1996 | WIPO . |

*Primary Examiner*—Jose' G. Dees
*Assistant Examiner*—Alton Pryor
*Attorney, Agent, or Firm*—Sughrue, Mion, Zinn, Macpeak & Seas, PLLC

[57] ABSTRACT

A safe medical powder with excellent performances which is a magnetosensitive powder for diagnosis, therapy, or drug delivery and which, even when placed in the body for a prolonged period, neither suffers a decrease in magnetic sensitivity nor releases ions, etc. The medical powder comprises a base particle of a ferromagnetic metal having thereon a coating layer, wherein at least the outside of the coating layer comprises a bioinert substance. Preferably, the coating layer comprising a bioinert substance comprises a layer comprises a hydrolysate of an alkoxide compound.

5 Claims, No Drawings

MEDICAL POWDER

TECHNICAL FIELD

The present invention relates to a magnetic medical powder. More particularly, this invention relates to a magnetic medical powder which is used as a drug carrier for drug delivery, an immunolatex, immunobeads, a medium for hyperthermia, etc.

BACKGROUND ART

A medical powder which comprises a polymeric microsphere obtained by a polymerization method, such as emulsion polymerization, soap-free emulsion polymerization, and having thereon an immobilized antigen or antibody, and which is used for diagnosis where its cohesiveness with an antigen or antibody as the substance to be detected is examined is conventionally known as an immunolatex. A technique of using a labeled antibody as the immobilized antibody in an immunolatex is used for heightening detectability in diagnosis. Also, a technique in which a drug is supported on an immnunolatex together with an antibody and this immunolatex is used for delivering the drug to, e.g., cancer cells having an antigen responsive to the supported antibody, is used.

Beads are more frequently used as drug carriers for drug delivery than latexes because they have the higher ability to support drugs. The term "beads" means polymeric microspheres having larger particle diameters than the latexes. Latexes have particle diameters in the range of about 100 Å to about submicron sizes (1 μm or less), while beads have particle diameters in the range of submicron sizes to several millimeters. The beads comprising a polymeric compound and having thereon an immobilized antigen or antibody are generally called immunobeads.

Beads comprising a polymeric compound which contain a drug embedded therein and have thereon an immobilized antibody are used for delivering the drug to a diseased part where a responsive antigen is present. Namely, these are a kind of drug delivery beads.

Although biodegradable natural polymeric compounds, i.e., gelatin, starch, fibrinogen, and the like, have been used as preferred bead materials for such drug delivery beads, they have drawbacks, for example, that particle diameter control is difficult, beads of constant quality are difficult to obtain, and storage is difficult. Consequently, use of synthetic or semisynthetic polymeric compounds is progressing.

The immobilization of an antigen or antibody on the latex particles or beads is accomplished, for example, by bonding the protein (constituent substance of the antigen or antibody) with a condensing agent, e.g., cyanogen bromide or carbodiimide, to a reactive group, e.g., a hydroxyl group, an amino group, or a carboxyl group, present on the main chain of the polymeric compound constituting the latex particles or beads or to such a reactive group incorporated as a side chain into the constituent polymeric compound through substitution.

Another known example of the fields where the immunobeads are utilized is the field of cell separation. An example of immunobead utilization in the field of cell separation is in therapy or diagnosis. In this application, magnetic immunobeads (hereinafter referred to also as "magnetosensitive immunobeads") are prepared by fixing a ferromagnetic substance to polymeric beads, for example, by incorporating an iron powder or another ferromagnetic material powder into the beads or embedding aggregates of ferromagnetic material powder particles in the beads and further immobilizing an antibody to the surface of the beads. The magnetosensitive immunobeads are introduced into the blood to allow the immunobeads to react with a responsive antigen (pathogenic antigen) present in the blood to thereby immobilize the antigen to the immunobeads. The magnetosensitive immunobeads are then collected with a magnet to thereby remove the antigen from the blood. The magnetosensitive immunobeads thus used for removing a pathogenic antigen from the blood are used also for removing tumor cells from bone marrow.

Still another use of magnetosensitive beads is in drug delivery. Specifically, magnetosensitive beads are used as a therapeutic powder in a drug delivery system in which the magnetosensitive beads are intravenously injected into a living body, e.g., human body, and a magnet or the like is externally applied to a diseased part to lead the drug-supporting magnetosensitive beads to the diseased part by means of magnetic induction. An example of these magnetosensitive beads is a medical powder comprising a polymeric microsphere which contains a magnetite as a base material embedded therein and simultaneously have a drug supported thereon.

Furthermore, a medical powder comprising a metallic conductor is used as a heating medium in the method of treatment called hyperthermia, in which a powder of a conductor such as a metal (a metal powder is generally used) is introduced into a part affected by terminal cancer and the affected part is burnt by high-frequency induction heating.

The current medical powder which comprise a polymeric microsphere containing a magnetite as a base material embedded therein and is used for the diagnostic-therapeutic system described above (i.e., one form of the magnetosensitive beads described above) employs a magnetite as a base material. However, since the magnetic force applied with current magnetic inductors is insufficient for these current medical powders, the locations of diseased parts to which the medical powders can be led are limited. There is hence a desire for a medical powder (i.e., magnetosensitive beads) having higher magnetic sensitivity.

Additionally, during long-term residence in a living body, the current magnetosensitive beads suffer changes such as, e.g., oxidation of the embedded base material and come to have reduced magnetic sensitivity. There have also been cases where ions such as iron ions are released from current magnetosensitive beads. Thus, the current magnetosensitive beads have the unsolved problems described above.

An object of the present invention is to eliminate the problems of the current magnetosensitive beads and to provide a safer medical powder which has excellent performances when used for the diagnosis, therapy, or drug delivery described above.

DISCLOSURE OF THE INVENTION

As a result of intensive studies, the above object has been found to be accomplished by the following medical powder of the present invention:

(1) A medical powder comprising a base particle of a ferromagnetic metal having thereon a coating layer, wherein at least the outside of the coating layer comprises a bioinert substance; and (2) The medical powder according to the above (1) wherein the coating layer comprising a bioinert substance contains a layer comprises a hydrolysate of an alkoxide compound.

The base particles of a ferromagnetic metal used in the medical powder, i.e., magnetosensitive beads, of the present invention are made of a ferromagnetic material preferably having a magnetization of 120 emu/g or more in a magnetic field of 10 kOe (kilo-oersted).

Examples of the ferromagnetic metal include pure iron, nickel metal, silicon steel, iron-nickel alloys, iron-cobalt alloys, iron-aluminum alloys, and iron-cobalt-nickel alloys, from the standpoints of high saturation magnetization, high magnetic permeability, and small coercive force. The iron and nickel are preferably ones obtained from the carbonyl compounds of iron and nickel, respectively. In particular, the iron obtained from carbonyl iron is more preferred from the standpoints of purity and profitability. Also, electrolytic iron and reduced iron can be used.

When a metal or alloy, such as the pure iron, nickel metal, or an iron-aluminum alloy, is exposed as it is to an aqueous solution containing an electrolyte such as unmodified blood plasma, it changes and comes to have a reduced magnetization and reduced magnetic permeability and to ionize and release ions. Accordingly, the surface of the base material in the present invention is coated with a bioinert substance in order to protect such changes of the base material.

The term "bioinert substance" herein means a substance which, even if exposed over long to an aqueous electrolyte solution, such as blood or another living-body tissue fluid, is not adversely influenced by the electrolyte solution to cause ion release, etc., and which, even if incorporated into a living body, does not exert any harmful physiological action.

Examples of the bioinert substance include organic polymers, for example, olefin oligomers (e.g., polystyrene, polypropylene, polybutene), vinyl oligomers (e.g., polyacrylic acid, polymethacrylic acid), diene oligomers (e.g., polybutadiene, polypentadiene, polychloroprene), and copolymers thereof; and metal oxides. Examples of the metal oxides include oxides of iron, nickel, chromium, titanium, aluminum, and silicon. A suitable kind of metal oxide is selected according to the property to be imparted to the surface of the powder. Although the thickness of each layer of the metal oxide film is not particularly limited, it is preferably in the range of 0.01 to 20 $\mu$m.

Organic polymers are advantageous in supporting a drug or an antigen or antibody thereon; on the other hand, metal oxides are advantageous in that they can effectively prevent a body fluid from penetrating therethrough and reaching the metallic base material.

Examples of methods for coating the surface of a base material with a metal oxide include methods of solid deposition in a liquid phase, such as electroplating and electroless plating, and methods of film formation in a gas phase, such as plasma-assisted CVD and plasma-assisted PVD. These methods can form a corrosion-resistant inorganic coating. Other examples include the method called a sol-gel method, in which a metal alkoxide is hydrolyzed in a solution. Since this sol-gel method can yield a coating layer which has an even thickness and is dense, it is suitable for use in the surface coating of a base powder for the purpose of preventing the base material from being changed by an aqueous solution containing an electrolyte, such as blood or another body fluid, as in the case of the base material in the present invention.

The sol-gel method based on the hydrolysis of a metal alkoxide is a process for powder coating with a metal oxide which comprises dispersing base particles into a solution of an alkoxide of the same metal as that of the metal oxide film to be deposited on the base particle surface, and hydrolyzing the metal alkoxide to thereby generate a sol of an oxide of the metal on the surface of the base particles. The sol generated deposits on the surface of the base particles and turns into a gel. Thus, a film of the metal oxide gel generates evenly on the base particles.

This method for powder coating with a metal oxide may be repeated to coat the base particles with layers of the same or different metal oxides, whereby a powder coated with a multilayered metal oxide film can be produced.

On the other hand, methods for coating the surface of base particles with an organic polymer film include the following methods besides the gas-phase surface polymerization of a base material and plasma-assisted CVD:

(1) a method in which base particles are emulsified or suspended in water together with a polymerizable monomer and emulsion polymerization or suspension polymerization is conducted respectively using an emulsion polymerization catalyst or a water-soluble polymerization catalyst, e.g., a catalyst such as ammonium persulfate, to obtain an organic-polymer coated powder as an emulsion polymerization or suspension polymerization product containing the base particles;

(2) a method in which the above-described emulsion polymerization or suspension polymerization product containing base particles is subjected as a base to seed polymerization to obtain an organic-polymer coated powder; and (3) other methods, for example, in which an organic-polymer coated powder is obtained by in situ polymerization.

Examples of the monomer for use in polymerization methods for coating the surface of base particles with an organic polymer film, e.g., in the emulsion polymerization, suspension polymerization, and seed polymerization described above, include the vinyl monomers and olefin monomers shown below. However, the monomers are not particularly limited thereto, and other monomers including oligomers and compounds modified with a polymerizable monomer are also usable.

Examples of ordinarily used polymerizable monomers include aryl-substituted vinyl monomers (for example, styrene, methylstyrene), unsaturated hydrocarbon monomers (for example, ethylene, propylene, butadiene, isoprene), and acrylic monomers (e.g., for example, acrylonitrile, (meth)acrylic esters, (meth)acrylamide, (meth)acrylic acid), vinyl acetate, maleic anhydride, and N-vinylpyrrolidone.

Organic polymers are preferred to metal oxides and the like as the material of the outermost layer of the medical powder to be injected into a living body, from the standpoint that organic polymers are more advantageous for supporting a drug or an antigen or antibody thereon. Consequently, a preferred embodiment of the medical powder of the present invention comprises a ferromagnetic material as a base material, a metal oxide film formed thereon which has a dense structure impermeable to water, ions, etc., and an organic polymer coating film formed on the outer side of the metal oxide film.

For example, the sol-gel method described above is used to deposit a silicon oxide film from a silicon alkoxide solution on a base made of pure iron, and a hydroxypropyl cellulose film is adsorbed thereonto as a substance-supporting film. The resultant particles are used as seeds to conduct seed polymerization in a monomer system comprising acrylic acid and styrene. Thus, medical beads each having a shell mainly comprising polystyrene can be produced.

After an antibody is immobilized on the polystyrene shells of the beads thus designed, the beads can be utilized as immunobeads for cell separation, etc.

If the magnetosensitive beads described above are used for drug delivery, a wide variety of drugs can be embedded in the polymeric beads, including carcinostatic agents, steroid agents, antibiotics, local anesthetics, and radioisotopes for radiation therapy. From the standpoint of facilitating the release of such an embedded drug in a diseased part, it is, for example, preferred to form the shells comprising an organic polymeric substance so as to have a multilayered structure or a composite phase and to fix a drug to the polymer part. It is also possible to apply an alternating magnetic field to accelerate drug release.

With respect to heating media for use in the above-described method of treatment called hyperthermia, in which a diseased part is burnt for treatment by high-frequency induction heating, no media having magnetosensitivity have been used so far. In this method of treatment, the introduction of the metallic conductor into a diseased part has been conducted through surgical incision or local injection, which is accompanied with much pain. However, by imparting magnetic sensitivity to a heating medium for hyperthermia, the heating medium can be introduced into the blood by intravenous injection, and the magnetic metallic conductor can be inducted to a diseased part by means of the magnetic induction caused by a magnetic field externally applied to the diseased part. Thus, the heating medium for hyperthermia can be introduced into the diseased part exceedingly easily. There is another advantage that by keeping a magnetic field being externally applied to the diseased part after the introduction, the heating medium can be prevented from diffusing from the diseased part with the lapse of time.

BEST MODES FOR CARRYING OUT THE INVENTION

The present invention will be explained in more detail by reference to Examples, but the invention should not be construed as being limited by the following Examples.
Production of Medical Powder

EXAMPLE 1

First Layer, Silica Coating

Into 100 ml of ethanol was dispersed 10 g of a powder of pure iron (carbonyl iron powder manufactured by BASF; average particle diameter, 1.8 μm; 201 emu/g at 10 kOe). The container was heated with an oil bath to keep the temperature of the liquid at 55° C. To this dispersion were added 6 g of silicon ethoxide, 6 g of 29% ammonia water, and 8 g of water. This mixture was allowed to react for 2 hours under stirring.

After the reaction, the reaction mixture was diluted and washed with ethanol and filtered. The solid matter was dried in a vacuum dryer at 110° C. for 3 hours. After the drying, the resultant powder was heated with a rotary tubular oven at 650° C. for 30 minutes to obtain silica coated powder $A_1$. The film thickness of the silica coated powder $A_1$ obtained was 75 nm. The powder was excellent in dispersed state.
Second Layer, Titania Coating After the heating, 10 g of the silica coated powder $A_1$ obtained was redispersed into 200 ml of ethanol. The container was heated with an oil bath to keep the temperature of the liquid at 55° C. To this dispersion was added 5 g of titanium ethoxide. This mixture was stirred. A solution prepared by mixing 30 ml of ethanol with 8.0 g of water was added dropwise to the above mixture over 60 minutes, and the resultant mixture was allowed to react for 2 hours. The particles were then vacuum-dried and heated to obtain titania-silica coated powder $A_2$. The titania-silica coated powder $A_2$ obtained was good dispersiblity, and was an independent particle. The titania film of this titania-silica coated powder $A_2$ had a thickness of 50 nm.
Third Layer, Polystyrene Coating To 600 g of distilled water was added 500 g of styrene monomer. While this mixture was heated to 70°C. under stirring, sodium lauryl sulfate was added thereto to emulsify the monomer. This emulsion was mixed with 25 g of the titania-silica coated powder $A_2$ whose surface had been lipophilized with methacrylic acid, and the resultant mixture was agitated at a high speed to sufficiently mix the ingredients. An aqueous ammonium persulfate solution was added thereto in an amount of 10% to initiate a polymerization reaction. The mixture was allowed to react for 4 hours under stirring. After completion of the reaction, the reaction mixture was diluted with 2 liters of distilled water, and the supernatant was discarded by decantation to collect the precipitate.

The precipitate was dried on a filter paper to obtain polystyrene-titania powder A. In a magnetic field of 10 kOe, the powder A obtained had a magnetization of 148 emu/g, which was about 1.5 times the magnetization of magnetite (90 emu/g) which had conventionally been used.
In Vivo Stability of Powder

EXAMPLE 2

In 500 ml of physiological saline held at 38° C. with an oil bath was immersed 10 g of the polystyrene-titania powder A for 24 hours.

As a result, the powder A underwent no change in appearance and no iron ions were detected in the physiological saline. Furthermore, the magnetization of the powder A in a magnetic field of 10 kOe after the immersion in physiological saline was 146 emu/g, which was almost the same as the magnetization value of 148 emu/g before the immersion.

COMPARATIVE EXAMPLE 1

On the other hand, 10 g of a powder B obtained by subjecting a powder of pure iron (carbonyl iron powder manufactured by BASF; average particle diameter, 1.8 μm; 201 emu/g at 10 kOe) to only the polystyrene coating described in Example 1 was immersed for 24 hours in 500 ml of physiological saline held at 38° C. with an oil bath in the same manner.

As a result, hydrogen generation was observed at 17 minutes after initiation of the immersion of the powder B. After 4 hours, a dark-brown powder and a black powder were observed. After 24 hours, the surface of the powder B had been completely oxidized and turned dark-brown, and the physiological saline had an iron ion concentration of 1.5%. The magnetization of the powder B in a magnetic field of 10 kOe, which had been 166 emu/g before the immersion in physiological saline, was 25 emu/g after the immersion. Namely, the magnetization thereof decreased to about 85% of the original value.

INDUSTRIAL APPLICABILITY

According to the present invention, a safe medical powder having excellent performances can be provided which, even if placed in the body for a prolonged period of time, neither suffers a decrease in magnetic sensitivity nor releases ions, etc.

Due to the medical powder provided by the present invention, not only magnetosensitive immunobeads having excellent performances can be provided to thereby greatly contribute to the field of cell separation, e.g., the separation of harmful cells from bone marrow, but also an excellent magnetically inducible drug can be provided to thereby greatly contribute to therapeutic fields, e.g., the field of drug delivery systems.

Furthermore, since the medical powder of the present invention can be easily produced, it can be supplied at low cost. The powder can be stored stably over long and can be supplied stably. Therefore, the present invention is highly effective also from the standpoint of profitability.

What is claimed is:

1. A medical powder comprising a base particle of a ferromagnetic metal having thereon at least one metal oxide layer, and an outside coating layer comprising bioinert substance, selected from the group consisting of polystyrene, polypropylene, polybutene, polyacrylic acid, polymethacrylic acid, polybutadiene polypentadiene, polychloroprene, and copolymers thereof, and a drug or medical component.

2. The medical powder according to claim 1, wherein the at least one metal oxide layer comprises a hydrolysate of an alkoxide compound.

3. The medical powder according to claim 1, wherein the metal oxide is selected from oxides of iron, nickel, chromium, titanium, aluminum and silicon.

4. The medical powder according to claim 1, wherein the drug or medical component is selected from the group consisting of an antigen, an antibody, a carcinostatic agent, a steroid agent, an antibiotic, a local anesthetic and a radioisotope for radiation therapy.

5. The medical powder according to claim 1, wherein the drug or medical component is releasable from the powder.

* * * * *